Figure 1:
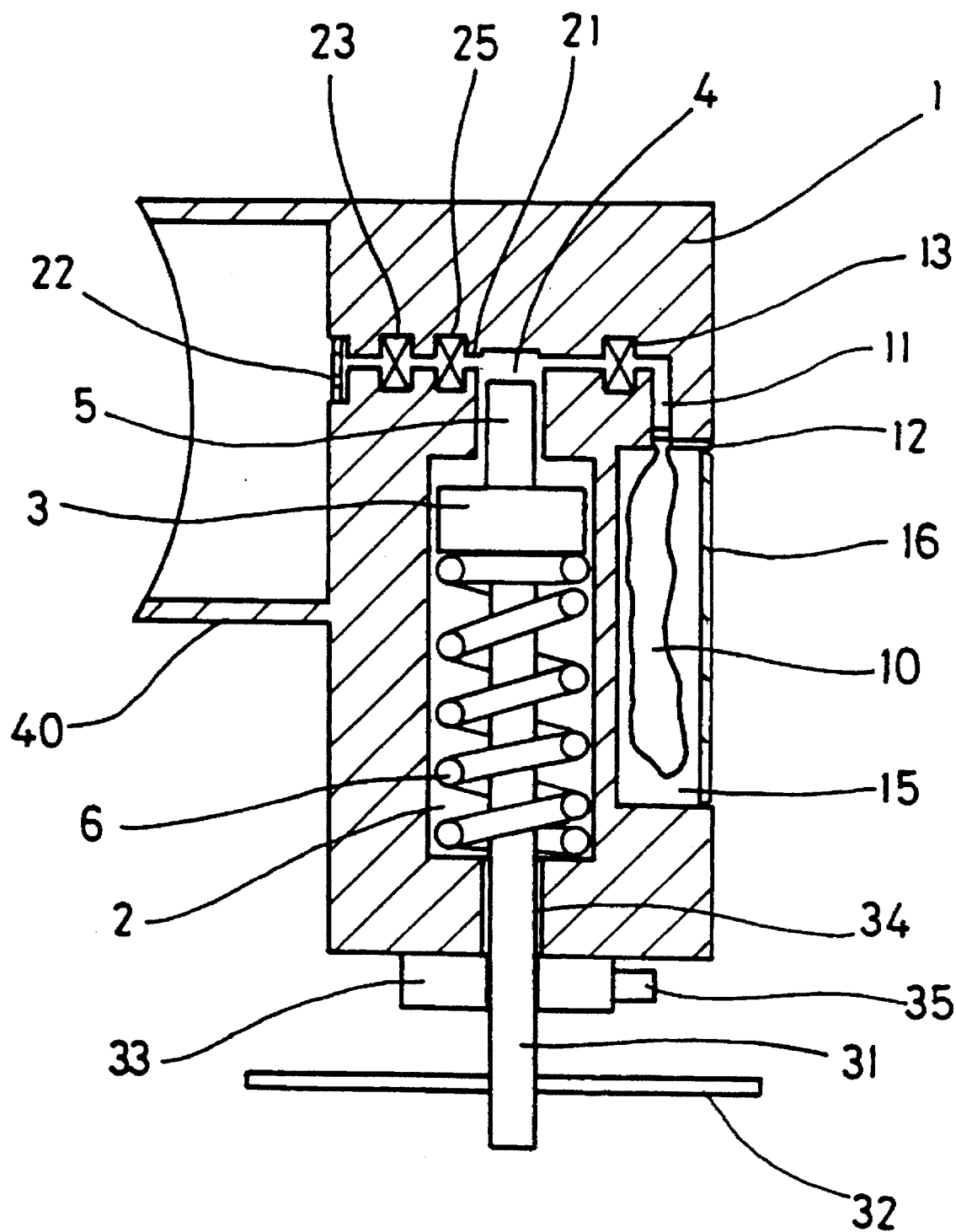

United States Patent [19]
Weston et al.

[11] Patent Number: 5,497,944
[45] Date of Patent: Mar. 12, 1996

[54] ATOMISING DEVICES AND METHODS

[75] Inventors: Terence E. Weston, Woodbridge; Stephen T. Dunne, Shotley, both of England

[73] Assignee: DMW (Technology) Limited, United Kingdom

[21] Appl. No.: 938,174

[22] PCT Filed: Mar. 21, 1991

[86] PCT No.: PCT/GB91/00433

§ 371 Date: Nov. 19, 1992

§ 102(e) Date: Nov. 19, 1992

[87] PCT Pub. No.: WO91/14468

PCT Pub. Date: Oct. 3, 1991

[30] Foreign Application Priority Data

Mar. 21, 1990 [GB] United Kingdom .............. 9006340
Nov. 1, 1990 [GB] United Kingdom .............. 9023767

[51] Int. Cl.$^6$ ............. A61M 11/00; B05B 11/00
[52] U.S. Cl. ............. 239/321; 222/321.1; 222/321.8; 222/383.1; 222/384
[58] Field of Search ................ 239/321, 518, 239/524, 543, 544; 222/321, 383, 384, 340, 341, 49, 321.1, 321.6–321.9, 383.1, 321.2

[56] References Cited

U.S. PATENT DOCUMENTS

| 334,110 | 1/1886 | Delaney . |
| 460,458 | 9/1891 | Bates . |

(List continued on next page.)

FOREIGN PATENT DOCUMENTS

| 21853/48 | 9/1948 | Australia . |
| 2017366 | 11/1990 | Canada . |
| 0086144 | 8/1983 | European Pat. Off. . |
| 0105964 | 4/1984 | European Pat. Off. . |
| 0111875 | 6/1984 | European Pat. Off. . |
| 0255208 | 2/1988 | European Pat. Off. . |
| 0379818 | 8/1990 | European Pat. Off. . |
| 2524348 | 10/1983 | France . |
| 1803541 | 4/1970 | Germany . |
| 63232866 | 9/1988 | Japan . |
| 992070 | 9/1981 | U.S.S.R. . |
| 405458 | 2/1934 | United Kingdom . |
| 931089 | 7/1963 | United Kingdom . |
| 1014685 | 12/1965 | United Kingdom . |
| 1131918 | 10/1968 | United Kingdom . |
| 1239855 | 7/1971 | United Kingdom . |
| 1279797 | 6/1972 | United Kingdom . |
| 1291367 | 10/1972 | United Kingdom . |
| 1389702 | 4/1975 | United Kingdom . |
| 1481199 | 7/1977 | United Kingdom . |
| 1493614 | 11/1977 | United Kingdom . |
| 1556977 | 12/1979 | United Kingdom . |
| 2041249 | 12/1982 | United Kingdom . |
| 2209564 | 5/1989 | United Kingdom . |
| WO87/04373 | 7/1987 | WIPO . |
| WO89/07244 | 8/1989 | WIPO . |
| WO91/16993 | 11/1991 | WIPO . |
| WO93/02729 | 2/1993 | WIPO . |

OTHER PUBLICATIONS

European Search Report for Application No. 94112017.2 dated Jan. 13, 1995 (3 pages).

*Primary Examiner*—Andres Kashnikow
*Attorney, Agent, or Firm*—Sterne, Kessler, Goldstein & Fox

[57] ABSTRACT

A metered dose inhaler for dispensing a fluid medicament as droplets of small mean particle size without the use of pressurized gas or liquefied propellants. A liquid drug is contained in a fluid reservoir, and metered quantities of the drug are successively presented into a reduced cross-section pressure chamber, with non-return valves controlling the flow of liquid through the device. The metered quantity of the drug is then subjected to a sudden and great increase in pressure by releasing a piston into the pressure chamber. The liquid drug is thereby ejected through an atomizing head, to reduce it to a fine atomized spray of small mean particle size, preferably less than approximately 12 micrometers.

76 Claims, 7 Drawing Sheets

U.S. PATENT DOCUMENTS

| | | |
|---|---|---|
| 1,035,261 | 8/1912 | Strumpf . |
| 1,116,536 | 11/1914 | Ballreich . |
| 1,276,245 | 8/1918 | Millard et al. . |
| 1,838,873 | 12/1931 | Scott . |
| 2,024,339 | 12/1935 | Connell . |
| 2,052,869 | 9/1936 | Coanda . |
| 2,187,779 | 1/1940 | Gardner . |
| 2,432,791 | 12/1947 | Osses . |
| 2,673,123 | 3/1954 | Benoit et al. . |
| 2,676,845 | 4/1954 | Rathsprecher . |
| 2,786,656 | 3/1957 | Corneil . |
| 3,187,748 | 6/1965 | Mitchell et al. . |
| 3,317,002 | 5/1967 | McKenzie ............................ 222/340 |
| 3,330,277 | 7/1967 | Gabriels . |
| 3,396,874 | 8/1968 | Malone . |
| 3,421,662 | 1/1969 | Hanson . |
| 3,471,065 | 10/1969 | Malone . |
| 3,575,322 | 4/1971 | Jordon . |
| 3,605,738 | 9/1971 | Ciranna . |
| 3,628,875 | 12/1971 | Wild . |
| 3,790,034 | 2/1974 | Horvath . |
| 3,794,247 | 2/1974 | Corsette . |
| 3,797,748 | 3/1974 | Nozawa et al. . |
| 3,831,861 | 8/1974 | Hanson, Jr. . |
| 3,838,686 | 10/1974 | Szekely . |
| 3,878,973 | 4/1975 | Riccio . |
| 3,893,628 | 7/1975 | McCollum . |
| 3,921,857 | 11/1975 | Riccio . |
| 3,921,861 | 11/1975 | Kondo . |
| 3,921,916 | 11/1975 | Bassous . |
| 3,923,202 | 12/1975 | Riccio . |
| 3,933,279 | 1/1976 | Maier . |
| 4,007,855 | 12/1977 | Hierath et al. . |
| 4,017,007 | 4/1977 | Riccio . |
| 4,079,865 | 3/1978 | Kutik . |
| 4,116,247 | 9/1978 | Zanasi . |
| 4,147,476 | 4/1979 | Warren . |
| 4,167,941 | 9/1979 | Capra et al. . |
| 4,174,055 | 11/1979 | Capra et al. ............................ 222/340 |
| 4,174,056 | 11/1979 | Loeffler ............................... 222/321 |
| 4,183,449 | 1/1980 | Blake . |
| 4,245,788 | 1/1981 | Wright . |
| 4,260,082 | 4/1981 | Rooney et al. . |
| 4,271,875 | 6/1981 | Meshberg . |
| 4,345,718 | 8/1982 | Horvath . |
| 4,391,620 | 7/1983 | Geisel . |
| 4,402,432 | 9/1983 | Corsette . |
| 4,412,632 | 11/1983 | Berger et al. . |
| 4,414,972 | 11/1983 | Young et al. . |
| 4,437,611 | 3/1984 | Gilroy . |
| 4,441,634 | 4/1984 | Meshberg . |
| 4,498,904 | 2/1985 | Turner et al. . |
| 4,506,497 | 3/1985 | Feuerlohn . |
| 4,534,345 | 8/1985 | Wetterlin . |
| 4,602,726 | 7/1986 | Goda ..................................... 222/321 |
| 4,615,469 | 10/1986 | Kishi et al. . |
| 4,648,393 | 3/1987 | Landis et al. . |
| 4,667,668 | 5/1987 | Watterlin . |
| 4,693,675 | 9/1987 | Venus, Jr. . |
| 4,694,977 | 9/1987 | Graf et al. . |
| 4,705,034 | 11/1987 | Perkins . |
| 4,810,659 | 3/1989 | Higo et al. . |
| 4,819,834 | 4/1989 | Thiel . |
| 4,828,184 | 5/1989 | Gardner et al. . |
| 4,860,738 | 8/1989 | Hegemann et al. . |
| 4,865,229 | 9/1989 | Schneider et al. . |
| 4,867,347 | 9/1989 | Wass et al. . |
| 4,875,605 | 10/1989 | Weston . |
| 4,892,232 | 1/1990 | Martin . |
| 4,896,832 | 1/1990 | Howlett . |
| 5,031,839 | 7/1991 | Waldrum ............................. 239/321 |
| 5,056,511 | 10/1991 | Ronge . |
| 5,088,649 | 2/1992 | Hanson et al. . |
| 5,115,981 | 5/1992 | Callahan et al. . |

ATOMISING DEVICES AND METHODS

The present invention relates to atomising devices and methods, notably to self contained hand held devices for dispensing a fluid medicament as droplets of a mean size less than about 10 to 12 micrometers without the use of pressurised gas or liquefied propellants, and to methods for administering fluid droplets to a locus, notably medicaments to the nasal passages or lungs.

BACKGROUND TO THE INVENTION

It is known to apply medicaments as sprays through the nose or mouth so that they are absorbed through the walls of the nasal passages or through the lungs. In order for the medicament to penetrate deep into the lung, for example into the alveolar sacs, it is considered necessary that the medicament particles or droplets have a mean size of less than 12 micrometers, for example from 1 to 5 micrometers. Whilst solid particles can be prepared with a mean size of less than 5 micrometers, problems are encountered in achieving such small sized droplets in a fluid spray.

Typically, such medicaments can be dispensed by means of bursts of large volumes of compressed air which entrain small amounts of the particulate to form a dust cloud or atomise some of a fluid to form a spray of fine droplets. However, this method results in losses of medicament and requires that the user have a source of large volumes of compressed air available and this is impractical except in a hospital environment.

For self contained hand held devices, it has been the common practice to dispense the medicament as droplets or solid particles using a liquefied propellant medium to dispense the droplets or particles from a pressurised container through a mechanical breakdown device, for example a swirl chamber and spray nozzle orifice. Whilst such a system enables a self contained and readily portable device to be constructed, the use of liquefied propellants is increasingly unacceptable from environmental and other grounds.

Thus, the use of chlorofluorocarbon type propellants (CFCs) is to be phased out for most uses under the Montreal Protocol of 1987 due to their alleged effect on the ozone layer of the atmosphere. However, despite this, it was considered that there was no viable alternative to the use of CFC propellants for medicaments, and their use in this field has been permitted to continue.

Furthermore, whilst it would be desirable to put up the medicament in the form of a solution to aid absorption of the active ingredient into the blood stream, many medicaments are insoluble in CFCs. In order to achieve a solution it is necessary to use co-solvents and surface-active agents which may introduce undesirable secondary components into the medicament formulation. Moreover, when such solutions are sprayed, the resultant droplets lose their CFC component through rapid evaporation. As a result, the user inhales droplets of varying sizes travelling at different speeds as their size changes. The rapid evaporation of CFCs also gives the disadvantage that the user experiencing an uncomfortable chilling effect as he inhales the spray. On the other hand, it is the very rapid evaporation of liquefied propellants which enables them to generate the high pressures within the dispenser required to discharge material from the dispenser.

Despite these problems with the use of CFCs, they are still considered by the pharmaceutical industry to be the only practicable method for administering many forms of medicament. As recently as March, 1990 a conference of leading experts in this field, the "Respiratory Drug Delivery II" Conference at Keystone, Colorado, U.S.A., did not contemplate that there was any other viable method of delivery for such drugs except the use of CFCs or their close analogues, such as the HFC and HCFC propellants.

In an attempt to overcome the problems associated with CFC propellants, there have been many proposals to adapt the mechanical pump type dispensers used to spray furniture polishes, hair lacquers and the like. In such devices a manually operated piston and cylinder or flexing diaphragm type of pump is operated by depressing an axial plunger or via a trigger type mechanism to force a fluid composition through a mechanical break up device, for example a swirl chamber and fine bore nozzle orifice, to form a spray of droplets without the use of a propellant gas or airstream. In general, the droplets formed are of a comparatively large size, typically 30 to 200 micrometers diameter; and the volume of the spray discharged at each operation of the pump is of little concern to the user.

In order for such devices to be suitable for use in dispensing a medicament, it is necessary to control both the droplet size, notably where the spray is to penetrate into the lungs of the user as stated above, and the amount of medicament dispensed so that each actuation of the pump will deliver a consistent dose of the medicament. It has therefore been proposed to incorporate some form of measured dose mechanism into the design of such pump spray devices. This is often provided in the form of the swept volume of the cylinder of the pump used to dispense the fluid, see for example U.S. Pat. Nos. 4,147,476 and 4,694,977 and PCT Application No WO 87/04373. However, where the user does not for any reason operate the pump mechanism for its full stroke, the amount of fluid dispensed can vary significantly from the desired dosage.

Furthermore, it has not hitherto been considered possible to achieve the required very small droplet size consistently. A conventional hand operated pump type sprayer is typically operated by the user manually depressing the free end of the pump housing or plunger or a trigger mechanism so as to discharge fluid held in the pump, for example from the cylinder of the pump as the piston of the pump is driven up the cylinder, see for example U.S. Pat. Nos. 3,838,686, 4,693,675 and 4,694,977. However, not only is the pressure generated by the pump comparatively low, but the pressure generated will depend upon the speed at which the pump is operated and the strength of the user. As a result, the droplet size in the spray varies from operation to operation, even with the same person operating the pump.

It has been proposed to provide a spring against which the pump mechanism acts as fluid is drawn into the pump on the sucking stroke of the pump, for example into the cylinder as the piston is retracted in a piston/cylinder type of pump, see for example U.S. Pat. Nos. 3,471,065, 3,790,034, 3,797,748, 4,260,082, 4,183,449 and 4,345,718. The spring then provides a consistent driving force when released to drive the fluid out of the pump. In these proposals, the pump is designed so that fluid cannot escape from the cylinder until a release or outlet valve is operated. Therefore, the fluid is held within the pump under the pressure exerted by the compressed spring. When the valve is operated, the fluid is discharged from the pump under the action of the spring. Although this achieves a greater uniformity of the pressure at which the fluid is discharged, the fluid may be held under pressure within the pump before the outlet valve is operated. This can result in a number of problems. For example, the pump mechanism and outlet valve must be designed to resist the substantial pressures generated by the compressed spring, otherwise leakage may occur or the pump cylinder walls may rupture. Furthermore, where the pressure is retained for any length of time, some seepage of the fluid past the seals in the pump mechanism, for example past the seals between the piston and the cylinder wall, will occur, resulting in a loss of fluid and pressure from the cylinder. This will affect the volume of fluid dispensed and the droplet size in the spray which is eventually produced when the outlet valve is actuated. A further problem arises in that the user may not operate the pump mechanism for its full stroke. This will not only affect the volume of fluid dispensed, but will also affect the peak pressure achieved and hence the droplet size, since the spring will not be fully compressed.

In an alternative form of device proposed in U.S. Pat. No. 4,892,232, the fluid is held under pressure in a main container and a pre-determined quantity is transferred to a distendable rubber or similar sleeve carried by the valve actuator stem of the outlet valve to the container. The stem is provided with suitable porting so that the sleeve is connected to the remainder of the container when the stem is in the raised position. Fluid will thus flow under pressure from the container into the annular space between the sleeve and the stem wall to expand the sleeve radially. When the valve stem is depressed, the porting to the remainder of the container is closed and a port is opened allowing the fluid to escape from the annular space to a nozzle orifice as the sleeve is stretched axially and collapsed radially. Again, this device suffers from the problems of variable dose and variable droplet size due to variations in the speed and force used by the user in the depression of the valve stem and the extent to which the valve stem is moved.

We have devised a form of atomizer device which reduces the above problems and does not use a liquefied propellant or gas stream to discharge the contents of the device. Whilst the device is of particular use in the application of medicament fluids to the nasal passages or to the lungs, it can be used to apply a wide range of other materials where a simple self contained readily portable device is required.

In a preferred embodiment of the device of the invention the user imparts energy to an energy storage means which is retained in the "loaded" state until required to act upon a measured dose of the fluid to discharge it through a mechanical break up device or other discharge means. The fluid need not be held under pressure in the device, thus reducing some of the problems associated with earlier proposals. Since the "loading" of the energy storage means can be interlinked with the measurement of the dose of fluid, the operation of a latch or other means for retaining of the energy storage means in its "loaded" state can be used to ensure that the correct dose of fluid is achieved. The device of the invention thus substantially eliminates the problems encountered with prior proposals and provides a simple and effective means for producing sprays of fine sized droplets without the need for pressurised or liquefied propellant gasses.

SUMMARY OF THE INVENTION

According to a first aspect of the present invention, there is provided a device for delivering a metered quantity of fluid as an atomised spray, preferably a spray of an aqueous solution of a medicament, which device comprises:

a. pressurising means for applying a predetermined amount of energy to a metered quantity of fluid in order to subject it to a predetermined increase in pressure; and b. atomising means for atomising the pressurised fluid.

Preferably, the device incorporates metering means for metering said quantity of fluid, and the atomising means is provided by a mechanical break up device through which the metered quantity of fluid is passed to atomise it when it is subjected to said increase in pressure.

In a preferred embodiment, the device of the invention comprises:

a. a pressure chamber provided with an inlet connection to supply liquid to said pressure chamber, and an outlet connection to receive pressurised liquid from said pressure chamber;

b. atomising means provided at or adjacent said outlet for causing said pressurised fluid to be atomised;

c. pressurising means comprising a pulse generating means for generating one or more pulses to subject fluid within said pressure chamber to at least one pre-determined increase in pressure; and d. interface means which is acted upon by said pulse(s) to vary the volume of said pressure chamber in order to increase the pressure in the chamber.

The device of the invention may further comprise one or more control means for controlling fluid flow between said pressure chamber, said inlet and said outlet.

Preferably, said pressure chamber comprises a cylinder within which a piston acting as the interface means is slideably journalled.

Preferably, said pulse generating means comprises an energy storage means and a releasing means for releasing energy from the energy storage means, thereby to generate at least one pulse from the energy storage means which acts on the interface means.

The device preferably also comprises loading means for loading the energy storage means; retaining means, for example a latch or other detent means, for retaining the energy storage means in a loaded state; and release means for releasing the retaining means, thereby to release the energy storage means so as to cause the metered quantity of fluid to be discharged through the atomising means as a spray of droplets.

Accordingly, from a preferred aspect, the present invention provides a device for dispensing a fluid as a spray of droplets to a locus, which device comprises:

a. means for receiving a pre-determined quantity of the fluid to be dispensed;

b. break up means in communication with said fluid receiving means and adapted to cause the fluid to be formed into a spray of droplets;

c. an energy storage means adapted to be actuated by a user of the device, preferably to store energy imparted thereto by the user during operation of the device, and to release a pre-determined amount of energy to the predetermined quantity of fluid in said fluid receiving means so as to subject said fluid to one or more pulses of a predetermined increase in pressure; and d. actuator means adapted to release said stored energy to act upon said pre-determined quantity of fluid and to cause said increase in pressure in said fluid so as to discharge said quantity of fluid via said break up means so as to form said spray of droplets of said fluid.

Preferably, the device of the invention comprises a piston in cylinder type pump mechanism, at least part of the bore of the cylinder acting as the pressure chamber adapted to receive a pre-determined quantity of fluid from a reservoir, preferably corresponding to the swept volume of the pressure chamber, upon actuation of the pump on its suction stroke. The piston acts as the interface means to transmit the energy pulse(s) to the fluid in the pressure chamber. It is also preferred that the operation of the pump be interlinked with the retaining of the energy storage means in the loaded state so that the user is required to operate the pump to its full or a predetermined extent in order to cause the retaining mechanism to engage. However, it will be appreciated that the retaining of the energy storage means may be transient and that the operation of the device may pass through the fully loaded state directly to the discharge cycle at which the energy in the storage means is released to discharge the fluid in the pressure chamber of the pump through the break up means to form the desired spray.

Preferably, the energy storage means takes the form of a compression spring. However, other forms of energy storage means can be used, for example a tension spring or bellows section to the wall of the cylinder, gas bulbs, motors, solenoids or a flexible or deformable membrane or diaphragm. In some of such energy storage means, for example a gas bulb or a motor or solenoid, the energy is already stored in the means or a battery associated therewith, and the user merely releases that energy when required. In other forms, for example a spring or flexible diaphragm, the user must impart energy to the energy storage means, i.e. must load the energy storage means, which energy is then released during operation of the device. For convenience, the invention will be described hereinafter in terms of a compression spring which is located substantially co-axially below the piston of a piston in cylinder type of pump so that operation of the pump on its suction stroke causes the spring to be compressed and thus store energy for the discharge stroke of the pump. If desired, more than one spring may be used. It is particularly preferred that the spring be at least partially pre-compressed so that the force applied by the spring as it expands does not vary greatly. The design and construction of the spring can be selected in known manner to achieve the pressure required in the pressure chamber during expansion of the spring on the discharge stroke of the pump.

The device of the invention is preferably put up in the form of a unit containing the operating mechanism of the device, for example the atomising means, the energy storage means and the fluid metering and pressure chambers; which unit can be mounted upon or can contain a removable reservoir for the fluid to be dispensed. Typically, the fluid will be contained in a collapsible container removably connected to the inlet to the pressure chamber or pump cylinder. Where large volumes of fluid are to be discharged, the reservoir can take the form of a discardable can, tube or the like onto the outlet of which the operative mechanism unit of the device of the invention is a screw, push or other fit. Part of the container can be used to provide part of the operative mechanism of the device of the invention. For example, the outlet tube of the container can be used to provide the piston of the piston in cylinder pump.

In order to achieve the high pressures required to form very fine droplets, for example less than 10 micrometers mean diameter, it will usually be necessary to provide some form of mechanical advantage in the energy loading mechanism and/or in the discharge mechanism of the pump.

Thus, it will usually be desired to provide a lever or cam mechanism to aid compression of the spring; and/or to step or otherwise reduce the diameter of the pressure chamber or the outlet from the pump cylinder so as to achieve an hydraulic pressure advantage at the inlet to the atomising means. Typically, the lever mechanism will take the form of a trigger type mechanism which the user operates single handedly with the spray outlet adjacent to and directed towards the locus to which the spray is to be applied. If desired, the spray outlet can incorporate a shroud or mouthpiece to aid directionality of the spray.

As indicated above, the lever or other mechanism preferably incorporates a latch or other retaining mechanism for retaining the spring or other energy storage means in the compressed or energy loaded state prior to initiation of the discharge cycle of the device. Such a retaining means can be a simple mechanical detent or latch which physically engages the spring or the pump mechanism and prevents release of the compression in the spring until some further operation is initiated. However, the retaining means may be provided by a stepped cam or over center type of mechanism which bears against the spring so as to hold the spring transitorily in the desired state of compression during the loading cycle, but which automatically releases the spring with continued operation of the device to discharge the fluid.

As indicated above, the device of the invention is of especial use in the formation of a spray of droplets of a medicament for inhalation by a patient. For such use it is desirable that the droplets have a mean diameter less than about 12 micrometers. However, the invention can be applied to spraying of a wide range of other materials in solution, emulsion, dispersion or suspension form to produce droplets with sizes of up to 200 micrometers or more. For convenience, the invention will be described hereinafter in terms of dispensing a spray of an aqueous solution of a medicament for inhalation into the lungs of a patient via the mouth.

For such use, the droplet size is desirably less than 10 micrometers, typically 2 to 6 micrometers. Such small droplet sizes can be achieved by atomising the fluid using a wide range of atomising or mechanical break up devices, for example ultra sonic blades, impingement of two jets of fluid or impaction of a jet or spray onto a baffle or the like. However, we prefer to form the spray by passing the fluid at high pressure through a small nozzle aperture, preferably in association with a swirl chamber or other device for causing a significant secondary flow in the fluid transverse to the main flow at the nozzle orifice. The optimum pressure and nozzle orifice shape and size can be determined for any given case using techniques known in the art. Thus, where very high pressures can be generated in the pump cylinder or pressure chamber, for example 300 to 500 bar, comparatively large nozzle orifice diameters can be used, for example up to 100 micrometers, typically greater than 30 to 50 micrometers. However, we prefer to operate the device of the invention with pressures of from 50 to 400 bar, preferably 100 to 350 bar; and with nozzle orifice of from 1 to 12 micrometers, notably 2 to 6 micrometers. If desired, the device of the invention can incorporate means to vary the pressure generated, for example by adjusting the extent of compression of the spring, and/or the diameter of the nozzle orifice. The pressure quoted herein are the absolute pressures achieved in the pressure chamber; and the nozzle orifice diameters are the effective hydraulic diameters.

Preferably, the atomising means comprises an outlet orifice mounted in or on a body, and the device of the invention further comprises a member which is moveable with respect to said body to initiate operation of said atomising or break up means, the arrangement being such that such movement of said member does not cause movement of said orifice. It is thus possible for a user to operate the device without moving the outlet nozzle, which is of benefit when applying a medicament through the mouth or nose. It is also preferred that, where the device of the invention is to be used as a Metered Dose Inhaler (MDI) for the application of a medicament to the lung, the device is provided with a shroud or mouthpiece surrounding the atomising nozzle so as to assist in containing and direction of the spray into the nose or mouth. The shroud or mouthpiece may also assist the user in inhaling the spray.

The device of the invention preferably incorporates one or more valve means or other control means for regulating the flow into and out of the pressure chamber or the pump cylinder. Thus, it will usually be necessary to provide a non-return valve on the inlet and outlet to the cylinder or pressure chamber so that fluid flows into the cylinder or pressure chamber only during the suction stroke of the pump; and fluid flows to the atomising means only when the pressure is applied to the fluid in the pressure chamber or pump cylinder. In order to reduce the risk of premature escape of fluid from the device, it may be preferred that the outlet be provided with a pressure release valve, typically set to open when a pressure in excess of 50 bar is achieved in the pressure chamber or the pump cylinder.

Alternatively, the flow to and from the pressure chamber or the pump cylinder can be controlled by a rotary or other valve mechanism which is interlinked with the operation of the trigger or other lever mechanism which is used to operate the pump and to load the energy storage means. Thus, the operating trigger can be pivotally mounted on a shaft which incorporates a rotary valve so that as the trigger is progressively depressed it not only operates the pump to suck fluid into the pump cylinder through the valve, but also compresses the spring to store energy, and rotates the valve so that the connection between the cylinder and the reservoir is shut off and the connection to the nozzle outlet opened prior to release of the spring, for example as a cam carried on the shaft goes over center.

It is also preferred that the device of the invention incorporate one or more separation members upstream of the nozzle orifice to redcuce the risk of blockage of the fine nozzle orifice by particulate material in aqueous or other solutions of medicaments to be applied to the lung. Thus, a fine mesh filter, a ceramic or fritted disc or the like can be incorporated into the nozzle chamber or in the outlet to the pressure chamber. Typically, the filter will have an effective aperture or mesh size which is about half the nozzle orifice diameter.

The device of the invention is operated by charging the pressure chamber with the required quantity of fluid; loading the energy storage means with the required amount of energy where this has not already been done as when a bulb of pressurised gas or a motor is used to drive the piston of the pump; and then releasing the energy to apply one or more pressure pulses to the fluid in the pressure chamber so as to eject it through the atomising means to form the desired spray of fluid.

In a yet another aspect, the invention therefore provides a method of delivering a metered quantity of fluid as an atomised spray, comprising the steps of applying a predetermined amount of energy to the metered quantity of fluid in order to subject it to a predetermined increased in pressure, and passing the pressurised fluid through an atomising means, thereby to atomise the fluid.

DESCRIPTION OF THE DRAWINGS

For a better understanding of the invention, and to show how the same may be carried into effect, it will now be described, by way of illustration only, with reference to the accompanying diagrammatic drawings, in which:

FIG. 1 is a sectional view of a Metered Dose Inhaler (MDI) according to the invention, with the fluid to be dispensed carried in a collapsible bag removably mounted in the device;

FIG. 2 is a view similar to FIG. 1, but with a product to be dispensed in a pressurised container;

FIG. 3 is a sectional view of part of an alternative Metered Dose Inhaler, in which a product to be dispensed is contained in a collapsible tube having a nozzle which serves as a piston;

FIG. 4 is a view similar to FIG. 3, showing an alternative pressurising arrangement;

FIG. 5 is an enlarged detail view of one example of an atomising orifice assembly:

FIG. 6 is an enlarged detail view of one example of a mechanical break-up orifice;

FIG. 7 illustrates, diagrammatically, an alternative atomising means; and

FIG. 8 illustrates, diagrammatically, another alternative atomising means.

In the Figures, like reference numerals denote like or corresponding parts.

DESCRIPTION OF THE PREFERRED EMBODIMENTS

The MDI shown in FIG. 1 comprises a body in which there is defined a cylinder 2 of circular cross-section, in which a piston 3 is mounted for reciprocating movement. The cylinder 2 communicates with a pressure chamber 4 of reduced cross-section. The piston 3 has a reduced diameter portion 5 which sealingly engages within the pressure chamber 4, by means of a plastic [e.g. PTFE or Nylon] sealing cap or ring provided on the piston portion 5. The seal may be formed integrally with the reduced diameter portion 5 of the piston—for example, as a cap, rib or bead.

A pre-loaded compression spring 6 is located in the cylinder 2, between the enlarged head of the piston 3 and an opposite end wall of the cylinder 2. An operating rod 31 is connected to the piston 3, and passes through the spring 6 and through a passageway 34 in the body 1, to protrude from the body 1. At or adjacent an end of the rod 31 there is provided a handle means 32 for moving the rod 31 and the piston 3. If desired, the end of rod 31 can be connected to a trigger mechanism or lever mechanism incorporating a mechanical advantage so that the user can readily operate the device against the compressive force of spring 6. A latching means 33 provided on the body engages with the rod 31, to latch the rod 31 in a loaded position, as illustrated in FIG. 1. An actuating button 35 is provided, for releasing the latching means 33.

Also defined within the body 1 is a cavity 15 in which there is located a collapsible bag 10 containing the product to be dispensed [e.g. a liquid drug]. A door 16 on the side of the body 1 may be opened, in order to exchange the collapsible bag 10. By means of a connector 12, the interior of the bag 10 communicates with an inlet passage 11 which, in turn, communicates with the pressure chamber 4 via a non-return valve 13.

Also connected to the pressure chamber 4 is an outlet passage 21 which extends from the pressure chamber 4 to an atomising head 22, via a non-return valve 23 and a pressure release valve 25.

Optionally, the body 1 is provided with a mouthpiece 40, which affords an atomization chamber around the atomising head 22.

In use of the MDI of FIG. 1, when the piston 3 is in the loaded position as illustrated in FIG. 1, the pressure chamber 4 is full of liquid which has been supplied from the bag 10, via the passage 11 and non-return valve 13. The compression spring 6, as mentioned above, is already pre-loaded when fitted in the cylinder 2. The loading of the spring is increased further by withdrawing the rod 31 and thereby the piston 3 to the loaded position that is illustrated in FIG. 1.

The rod 31 is latched in its loaded position as illustrated in FIG. 1, by the latching means 33. Upon depressing the actuating button 35, the latching means 33 is released, thereby allowing the piston 3 to move suddenly forward under the force of the compression spring 6, to impart a sudden pressure pulse to the liquid in the pressure chamber 4.

The pressure in the liquid in the pressure chamber 4 therefore quickly builds up to exceed the limit value of the pressure release valve 25, and the liquid is then ejected under high pressure through the outlet passage 21 to the atomising head 22, via the one-way valve 23. During the forward travel of the piston 3, the non-return valve 13 prevents liquid from being returned to the bag 10, via the inlet passage 11. As the liquid is ejected through the atomising head 22, it is atomised into a fine spray, which can then be inhaled. The optional mouthpiece 40 provides an atomization chamber within which the fine spray is enclosed, and facilitates the inhalation of the spray.

To reload the MDI, the rod 31 is pulled back by means of the handle 32 against the resilient bias of the spring 6 and, at the end of its travel, the latching means 33 automatically latches the rod 31 into a latched end position. During this travel of the piston 3, liquid is sucked out of the collapsible bag 10 into the pressure chamber 4, via the inlet passage 11 and one-way valve 13. At this time, the one-way valve 23 prevents air being sucked into the pressure chamber 4 via the outlet passage 21. Due to the latching of rod 31, the fluid in pressure chamber 4 is held at ambient pressure and there is little or no risk of loss of fluid from the chamber. The operation of latching means 33 provides the user with a clear indication when piston 3 has completed the desired travel within cylinder 2 and that the required dose of fluid has been taken up. If the user fails to withdraw rod 31 to a sufficient extent, the latching means 33 will not engage and the user will detect the spring bias from spring 6 and will know to withdraw rod 31 further. The latching means 33 thus provides both the means for holding fluid in chamber 4 under ambient pressure and a means for alerting the user to incomplete operation of the device, hence reducing the risk of variable operation of the device.

Thus, the MDI is again in a loaded position, as illustrated in FIG. 1, ready for firing.

It will be appreciated that, in use of the MDI illustrated in FIG. 1, a metered dose of liquid product is pressurised and atomised in a highly accurate and repeatable manner. When the rod 31 and piston 3 are withdrawn to their loaded position, an exact metered quantity of liquid product is drawn into the pressure chamber 4. Upon releasing the latching means 33, the piston 3 is urged forwardly to impart a predetermined amount of energy to the liquid, and thereby increase its pressure by a predetermined amount. Thus, as the pressurised liquid is then ejected through the atomising head 22 of predetermined atomising characteristics, the liquid is atomised to a fine spray of predetermined mean particle size without the use of liquefied propellant or other gases.

In order to atomise the liquid to a very fine spray—for example, having a mean particle size in the range 1 to 12 micrometers—a very high pressure has to be applied to the liquid in the pressure chamber 4. By way of example, the capacity of the pressure chamber 4 may be 20 microliters; the diameter of the small end 5 of the piston 3 may be 2 mm; the diameter of the cylinder 2 may be 15 mm; the force of the spring 6 may be 100 Newtons; and the atomising head 22 may have an exit orifice of a diameter or the order of 3 to 15 micrometers. In such an arrangement, a pressure of the order of 400 bar may be generated in the liquid in the pressure chamber 4.

The cavity 15 may be open to atmosphere and at atmospheric pressure. In an alternative embodiment, the cavity 15 may be pressurised above atmospheric pressure, which helps to force the contents of the collapsible bag 10 into the pressure chamber 4, without the need to create subatmospheric pressures in the pressure chamber 4. This can help to avoid the formation of gas bubbles in liquid sucked into the pressure chamber 4.

The pressure release valve 25 may be optional; it may be omitted if desired. The pressure release valve 25 and non-return valve 23 may be combined as a single unit (not shown). It will be appreciated that the illustration of FIG. 1 is essentially diagrammatic in nature. A practical embodiment may be of different construction. For example, a lever or other gearing mechanism may be employed to assist loading of the piston 3 against the force of the spring 6. In one example, the MDI may be provided with a cover which, when opened, automatically loads the piston 3 and latches the latching means 33, so that the MDI is then ready for firing. The MDI would be fired by actuating the button 35, when the cover was open. In an alternative arrangement, the piston 3 may be loaded against the spring 6 and the latching means 33 latched, whilst a cover of the MDI is being closed. Thus, the device would be pre-loaded and may be fired straight away, upon opening the cover. In another variation, opening of a cover of the device may automatically load the piston 3 against the force of the spring 6, latch the latching means 33, and then automatically released the latching means 33 at the end of the action of the opening cover so that the latching is only transient.

The MDI of FIG. 1 is preferably of small, pocket size. Since, in contrast to known MDIs, it does not have to provide an appreciable volume to contain a liquified gas propellent under pressure it can readily be made of small dimensions. Despite this, the product container, in the form of the collapsible bag 10, can contain much more medicament than conventional MDIs. For example, whereas conventional MDIs might be limited to 200 to 400 doses, an MDI constructed along the lines illustrated in FIG. 1 may readily contain 1,000 or more doses, in the collapsible bag 10. As will be appreciated, the contents of the bag 10 are protected from contamination by the atmosphere and the operation of the device of the invention is by way of atomization of the fluid in chamber 4 without the use of an air blast, i.e., the device of the invention operates as an airless sprayer.

When the bag 10 is empty, it may simply be removed from the cavity 15 and replaced with a fresh bag. Preferably, the bag 10 includes a seal to prevent the escape of product from the bag 10, unless the bag 10 is connected to a connector such as 12.

In alternative embodiments, part of the piston and/or valve arrangement may be made disposable, together with the product container such as the collapsible bag 10.

It is to be appreciated that, in use of the illustrated MDI, there is nothing [short of catastrophic failure of the apparatus]to stop the discharge of the contents of the pressure chamber 4 as an atomised spray, once the actuating button 35 has been depressed to release the latching means 33 and thereby release the spring 6. Thus, the amount of energy applied by the spring 6 to the metered quantity of liquid in the pressure chamber 4 is absolutely predetermined, so that the increase in pressure to which the metered quantity of liquid is subjected is likewise absolutely predetermined. This objective is to be realised in all other illustrated embodiments of the invention described below.

Another feature of the MDI of FIG. 1 is that the metered quantity of liquid in the pressure chamber 4 is subjected to an increase in pressure only when the actuating button 35 has been depressed to release the latching means 33 and thereby release the spring 6. This has the advantage that no seals or other means are required to constrain the highly pressurised liquid, prior to the atomization stroke. The increase in pressure applied by spring 6 and piston 3 to the metered quantity of liquid in the pressure chamber 4 causes the pressurised liquid to pass through the atomising head 22, to be atomised thereby. This objective is to be realised in all other illustrated embodiments on the invention described below.

Another important advantage of the MDI of FIG. 1 is that, upon depressing the actuating button 35 to release the latching means 33 and spring 6, the atomising head 22 does not move within the body 1—only the button 35 moves. This facilitates accurate direction of the atomised spray, and contrasts with a conventional vertical-axis finger pump arrangement, in which the atomising nozzle itself is depressed to initiate atomization. This would be inconvenient in a medical inhaler, since it would be difficult to direct the spray accurately. Again, this objective is to be realised in all other illustrated embodiments of the invention described below.

Figure 2:
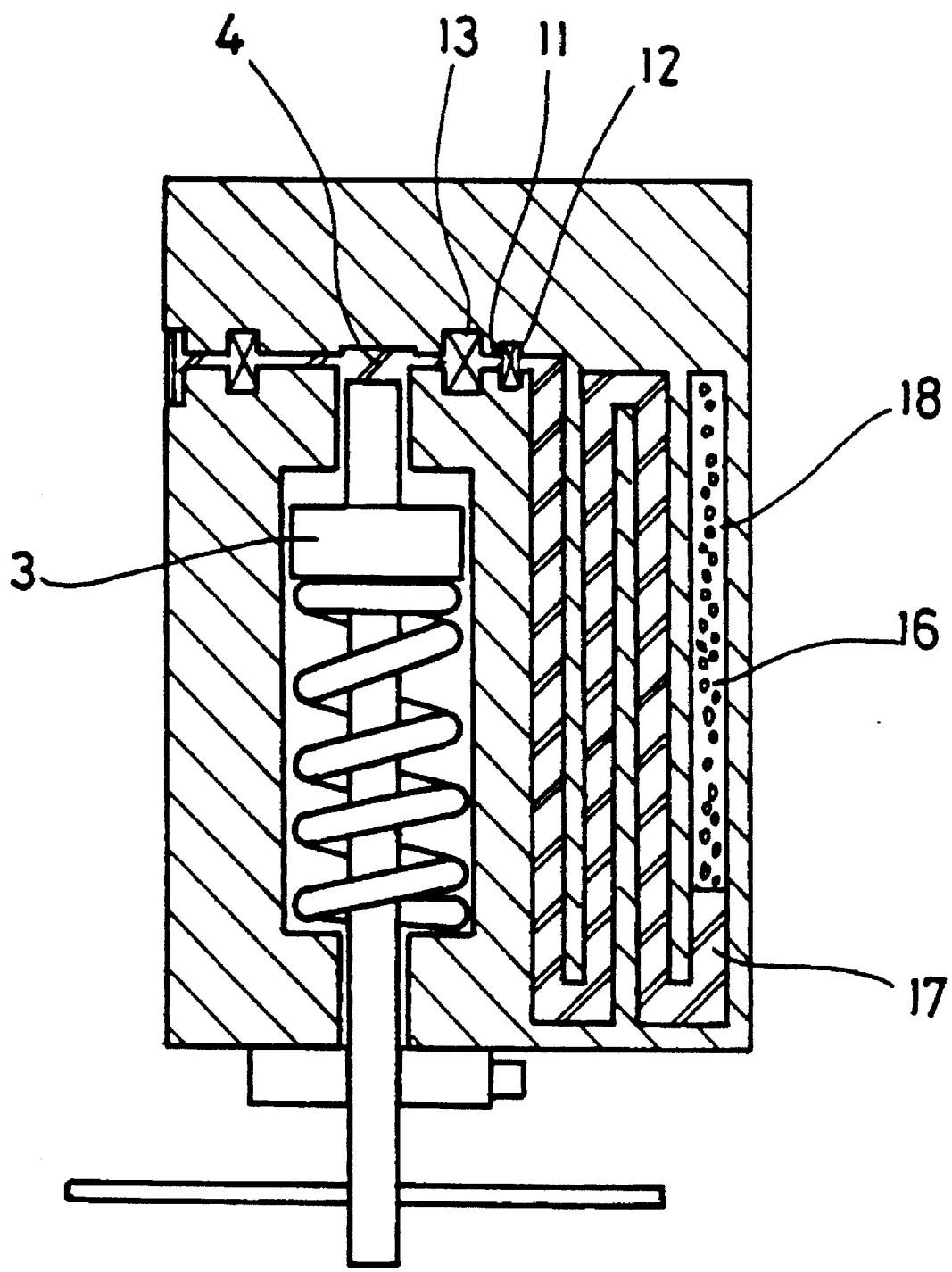

The MDI illustrated in FIG. 2 is generally similar to that of FIG. 1. However, in FIG. 2, the pressure release valve 25 is not provided. Also, the product container comprises a long tube 16 in which liquid product 17 is stored under pressure, which is created by a reservoir of gas 18 stored behind the liquid 17. As the piston 3 is pulled back to a loaded position, liquid product 17 is forced into the pressure chamber 4 via the inlet passage 11 and non-return valve 13, under the pressure of the gas 18. As the liquid product 17 is used, the gas 18 expands into the tube 16, pushing the liquid product 17 ahead and losing some pressure. The initial pressure of the gas 18 should be sufficient to maintain a pressure above atmospheric, until all of the liquid product 17 is used up.

The pressure tube 16 may be made as a replaceable item, for exchange in the MDI when the liquid product 17 is used up. Alternatively, the whole MDI may be manufactured quite cheaply of principally plastics parts, such that it may be a throw-away item. If the tube 16 is at least partly visible from the outside of the MDI, a visual check may be provided, as to the level of product remaining.

In the embodiments of FIGS. 1 and 2, the spray action is initiated by actuating of the button 35. In an alternative arrangement, the latching mechanism 33 may be released automatically in response to a user inhaling adjacent the atomising head 22. For example, a mouthpiece such as 40 may be connected to a vane that is caused to move by pressure difference across it when a user inhales, and thereby release the latching mechanism 33 to initiate the spray. Such automatic actuating mechanisms are known in themselves, in existing MDIs.

In the embodiments of FIGS. 1 and 2, the stroke of the piston 3 is fixed. If desired, means may be provided for varying the stroke of the piston. Preferably, such means is calibrated, so that a user may optionally adjust the MDI to dispense differing quantities of spray. However, it will be appreciated that, in every case, once the adjustment means has been set to a particular value, the MDI will then provide a metered dose of spray in a highly repeatable manner, just as if the stroke of the piston were fixed.

It will be appreciated that the devices of FIGS. 1 and 2 have been described above in terms of a device in which the cylinder of the pump mechanism is static and the piston moves axially therein. However, it is within the scope of the present invention to carry the cylinder upon the rod 31 and to have the piston fixed.

Figure 3:
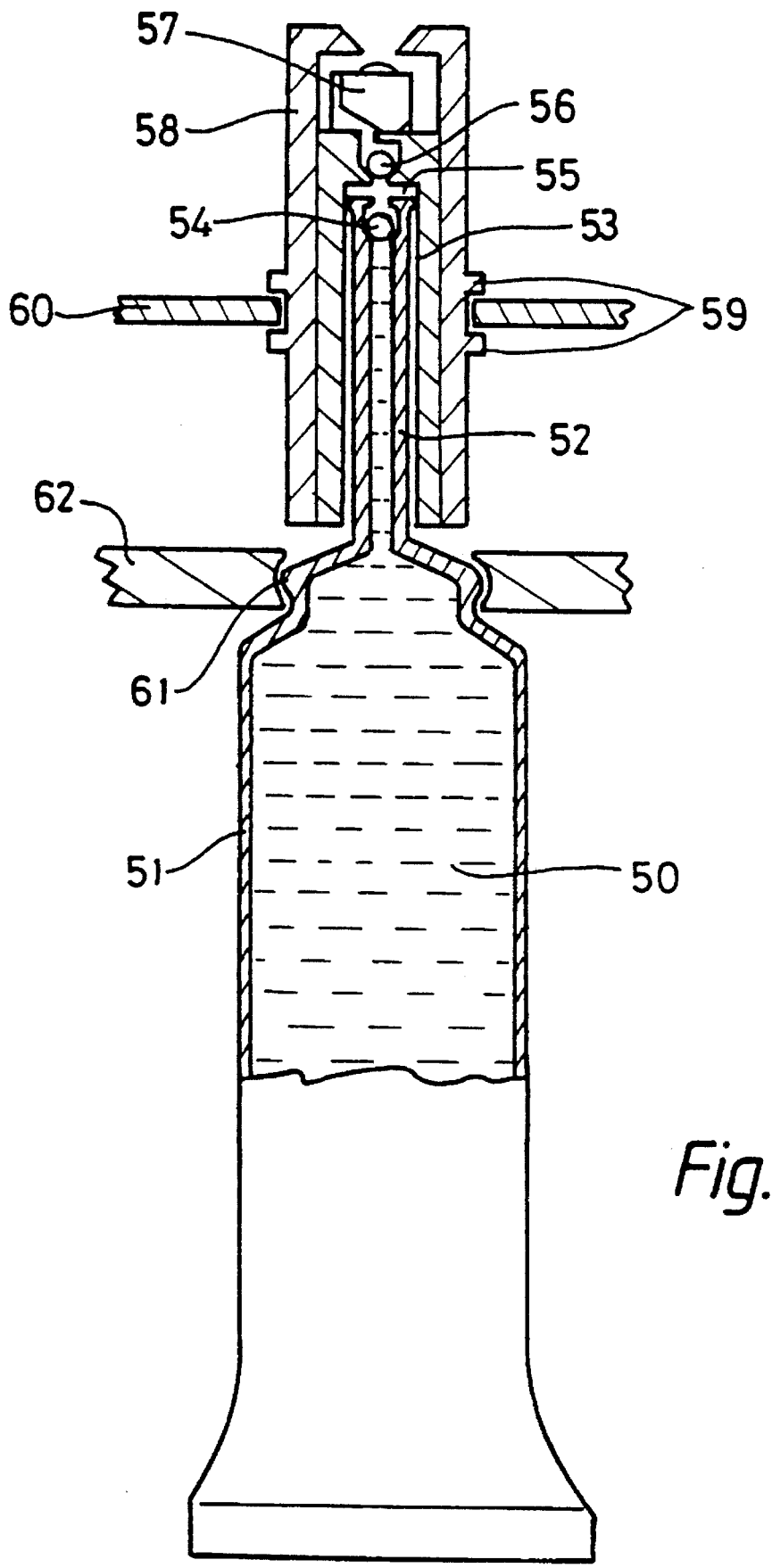

In the embodiment illustrated in FIG. 3, a liquid product 50 is contained within a collapsible tube 51 which is formed integrally with an extended nozzle 52 which serves as a piston. The nozzle/piston 52 is located for reciprocating movement within a cylinder 53. At the end of the nozzle/piston 52 there is incorporated a simple non-return valve 54. A pressure chamber 55 is defined at the end of the cylinder 53, and communicates via a simple non-return valve 56 with an atomising head 57.

The cylinder 53, non-return valve 56 and atomising head 57 are all contained within a casing 58, which is formed with annular ribs 59, which serve to locate the casing 58 in a first main body part 60.

The top of the product tube 51 is formed with an annular rib 61, which serves to locate the tube 51 in a second main body part 62. Resilient bias means is provided for urging the two main body parts 60 and 62 towards one another. A latching means is provided for latching the two main body parts 60, 62 at a predetermined distance apart, in a loaded condition, and actuating mean is provided for releasing the latching means. In the interests of clarity, the resilient bias means, latching means and actuating means have not been shown in FIG. 3, but, of course, examples of these have already been shown in FIGS. 1 and 2.

The embodiment of FIG. 3 operates as follows: as illustrated in FIG. 3, the MDI is in an unloaded or "fired" condition. By means of a suitable mechanism, the main body parts 60 and 62 are moved away from one another, to cause the nozzle/piston 52 to withdraw relative to the cylinder 53. The depressurisation in the pressure chamber 55 thereby causes the liquid product 50 to be sucked out of the tube 51, via the non-return valve 54, to fill the pressure chamber 55. During this action, the non-return valve 56 serves to prevent air from entering the pressure chamber 55 from the atomising assembly 57.

At the end of the loading stroke, the latching means operates to hold the main body parts 60, 62 apart at predetermined relative positions. Upon releasing the latching means by the actuating means, the nozzle/piston 52 is suddenly urged under the action of the resilient bias means into the cylinder 53, to apply sudden pressure to the liquid product 50 in the pressure chamber 55, in a manner generally similar to that in the embodiments of FIGS. 1 and 2. The pressurised liquid product is then ejected under pressure into the atomising assembly 57, via the non-return valve 56, and is then atomised into a fine spray by the atomising assembly 57.

The MDI is then reloaded by the respective lever mechanism to move apart again the two main body parts 60, 62, against the force of the resilient bias means.

Thus, it will be appreciated that the embodiment of FIG. 3 operates in a generally similar manner to the embodiments of FIGS. 1 and 2. However, in FIG. 3, the product 50 is provided in a particularly convenient manner in the product tube 51 which, together with the nozzle/piston 52 and the built in simple non-return valve 54, may be exchanged as a complete throw-away unit. It will be appreciated that the product tube 51 and its integral nozzle 52 and non-return valve 54 may readily be manufactured in a relatively economical manner out of plastics materials. The user is protected from contact with the liquid product 50, except when the MDI is properly actuated. Features of the embodiments of FIGS. 1 and 2, including variations as discussed above, may be provided, where appropriate, in combination with features of the embodiment of FIG. 3.

In the embodiment of FIG. 3, either of the parts 60, 62 may be fixed in relation to a main body of the MDI, the other of the parts 60, 62 then being moveable with respect to the fixed part. Alternatively, both parts 60, 62 may be moveable with respect to a main body of the MDI.

Figure 4:
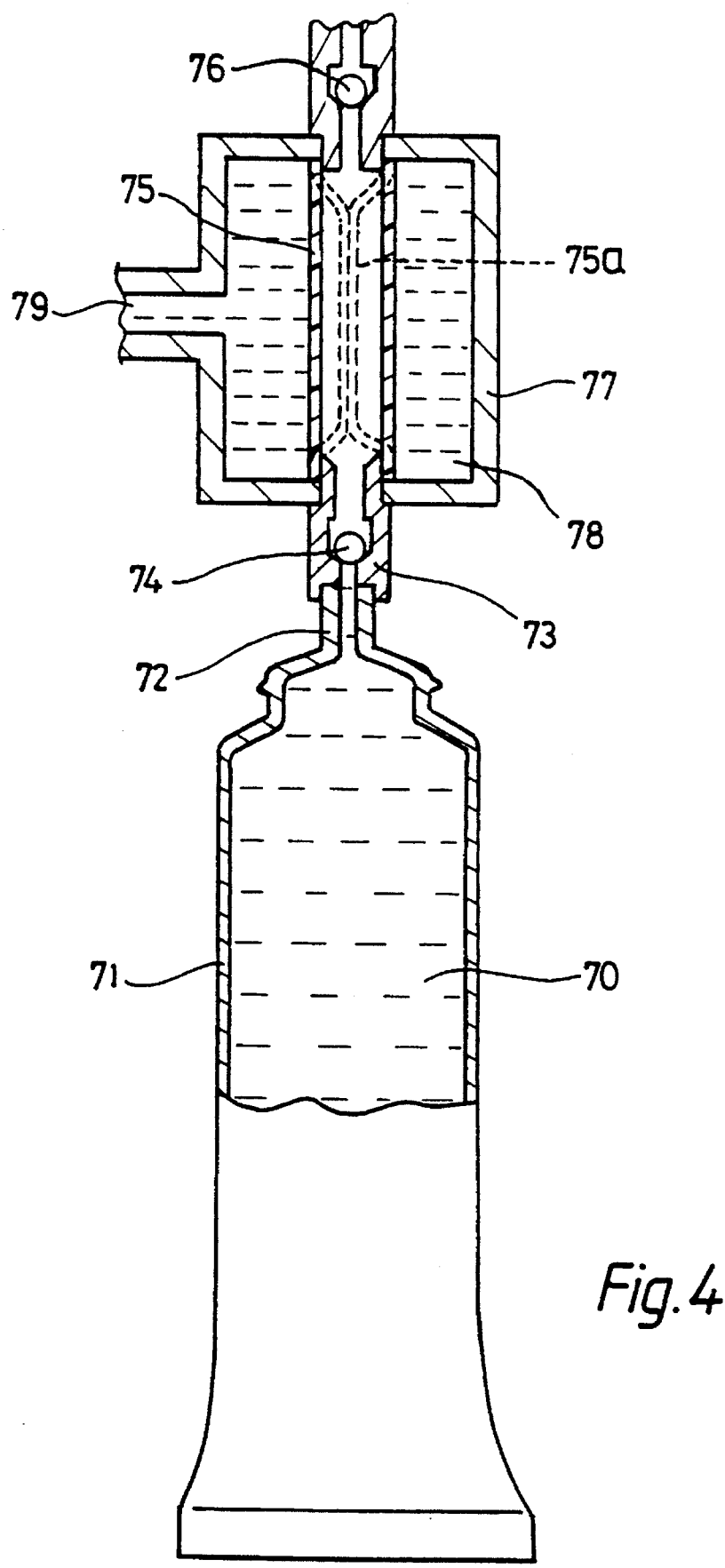

In the embodiment of FIG. 4, liquid product 70 is contained within a collapsible tube 71. A nozzle 72 of the tube 71 connects with an inlet passage 73 which contains a non-return valve 74. The non-return valve 74 communicates with a flexible tube 75, which may flex between a "full" position [illustrated in solid lines] and an "empty" position 75a [illustrated in broken lines]. The flexible tube 75 communicates with another non-return valve 76 which, in turn, communicates with an atomising head [not 10 shown]. The flexible tube 75 is contained within a pressure chamber 77 which is filled with a secondary liquid 78. The secondary liquid 78 communicates with a pressure pulse generator [not shown] via a passage 79. The embodiment of FIG. 4 operates as follows: when a flexible tube 75 is in its "full" position, it is full of liquid product 70 sucked from the collapsible tube 71. Upon applying a pressure pulse to the secondary liquid 78, the pressure in the pressure chamber 77 suddenly increases, and this causes the flexible tube 75 to be urged into its "empty" position 75a, during which action the liquid product within the tube 75 is expelled out of the non-return valve 76 to the atomising head [not shown] under high pressure, such that the atomising head atomises the liquid product into a fine spray, generally as in the preceding embodiment.

At the end of the pressure pulse, the flexible tube 75 resumes its initial "full" position and, during this action, liquid product 70 is sucked up from the collapsible tube 71, via the non-return valve 74, into the space within the flexible tube 75. The flexible tube 75 may return to its "full" position under its own natural resilience. Alternatively or additionally, it may be assisted in this by the application of a negative or reduced pressure pulse to the secondary liquid 78 in the pressure chamber 77.

The pressure pulses in the secondary liquid 78 may be generated by any suitable means. However, it is important that the pressure pulses are of a predetermined amplitude and duration to ensure that a metered dose of liquid is repeatedly sucked into the flexible tube 75 and subsequently expelled therefrom under a predetermined pressure increase, to produce a repeatable spray through the atomising head.

By way of example, the pressure pulse generator may include a piston and cylinder arrangement, together with latching and actuation means, of a type generally similar to that illustrated in FIGS. 1 and 2.

Typically, the pressure pulses may be of substantially square wave form. However, if desired, the pressure pulses may be of any predetermined shape—for example, if a time-varying spray spectrum were deliberately chosen. The important factor is that whatever the shape of the pulses, they are accurately repeatable. This may apply to all embodiments.

Figure 5:
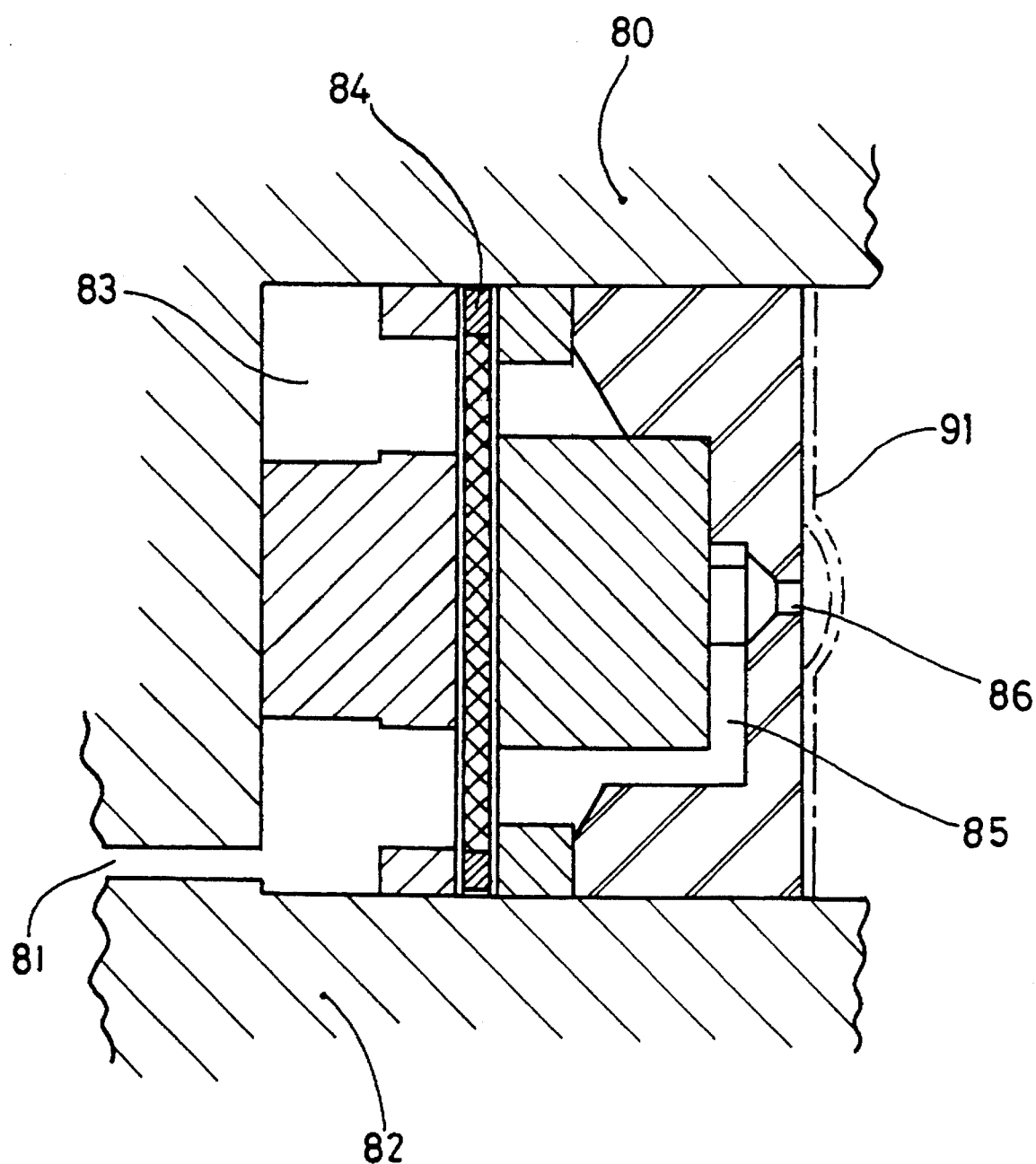

FIG. 5 shows, in enlarged detail, one example of an atomising head assembly 80. An inlet passage 81 formed in a body 82 leads to an inlet chamber 83. Interposed between successive sections of the inlet chamber 83 is a filter 84. The final section of the inlet chamber 83 leads to swirl chamber 85 which, in turn, leads to a nozzle 86.

The purpose of the filter 84 is to prevent particles from blocking the final orifice. For example, the filter 84 may be made of stainless steel mesh, having a mesh size in the range 1 to 10 micrometers—preferably, 3 micrometers.

Figure 6:
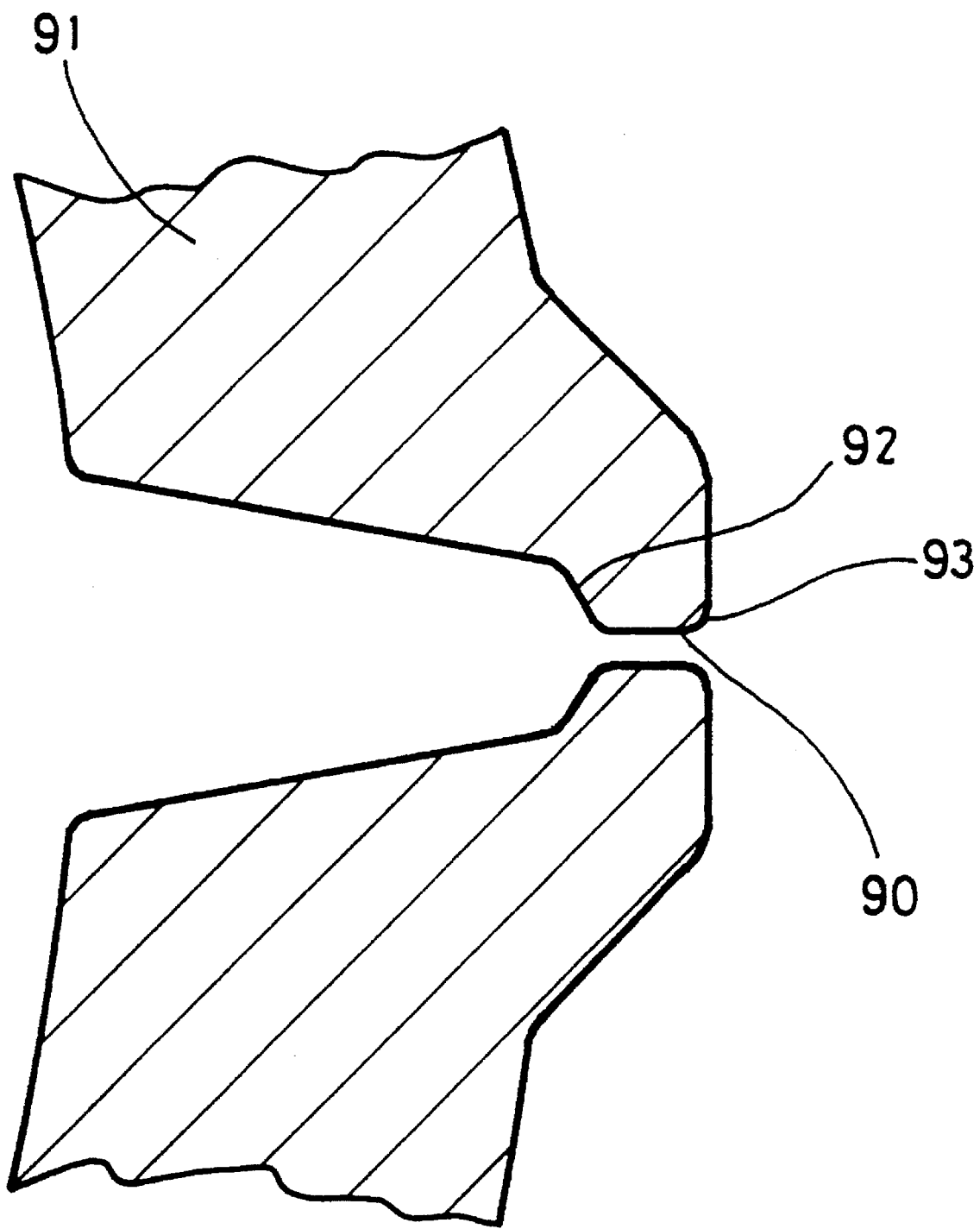

FIG. 6 shows one example of an atomising orifice 90, which is formed in a plate 91 which may be positioned, for example, downstream of the atomising nozzle 86 in the assembly of FIG. 5, as shown by chain-dot lines in that Figure.

As may be seen in FIG. 6, the final exit orifice 90 has a diameter of 6 micrometers, and an overall length of 30 micrometers, to include an inwardly tapering throat 92 at an angle of 30° to normal and an outwardly flared mouth 93. The orifice plate 91 has a thickness of the order of 1 mm, and a tapering inlet passage has a length of about 1 mm, tapering at an angle of 20° from an initial entry orifice size of 70 micrometers. Using a final atomising orifice of the order of 6 micrometers, together with a high pressure applied to the liquid to be atomised [by means of the energy store such as the compression spring 6, etc], can lead to a very effective and uniform mean particle size of the eventual spray. Tests with an exit orifice of the order of 6 micrometers, as illustrated in FIG. 6, together with a liquid pressure of the order of 300 bars, has produced a uniform spray of mean particle size of the order 5–8 micrometers. Preferably, the diameter of the exit orifice 90 is less than 100 micrometers. The preferred range for its diameter is 1–20 micrometers and the most preferred range is 3–10 micrometers.

The exit orifice 90 may be formed by piercing the plate 91— for example, by means of a tungsten carbide needle [e.g. similar to those used in forming spinarettes in the textile industry] or by any other suitable method.

Figure 7:
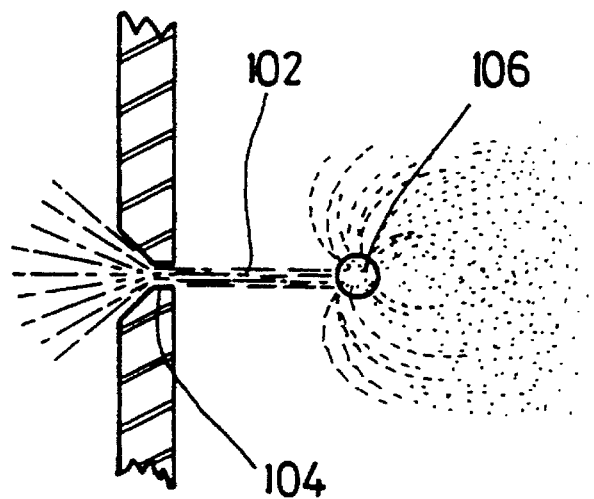
Figure 8:
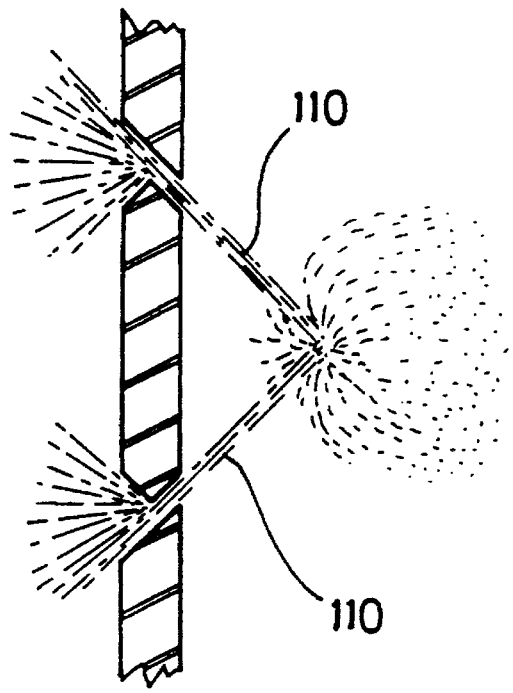

Although it is preferred to use a small bore nozzle orifice to achieve atomization of the fluid, it is possible to use alternative atomising means. For example, as shown in FIG. 7, a liquid jet 102 may be produced through an exit orifice 104 to impinge at high velocity upon an object such as a metal ball 106, which then causes the liquid to atomise. Another alternative arrangement is shown in FIG. 8, where two liquid jets 110 at high velocity and pressure are caused to meet, such that the liquid becomes atomised at their meeting point.

Initial experiments with MDIs having constructions along the lines of at least some of the embodiments illustrated herein have proved to be surprisingly effective, readily providing repeatable spray doses of drugs having a mean particle size less that 30 micrometers and typically of the order of 3–10 micrometers. Mean particle sizes in the range 2–8 micrometers or less than 5 micrometers may be preferred. A particularly important aspect of such embodiments of the invention is that the drug can be used immediately in its water soluble form. Many drugs used at present have two formulations—one for use in an MDI, and the other for use in nebulizers usually used in hospitals. The latter formulation is almost always an aqueous solution of the drug, so such formulations are immediately available for use with embodiments of the present invention.

By enabling application of drugs in aqueous solution with MDIs embodying the invention, new drug development may be accelerated. This is because much of the present long term testing is to ensure that the propellant (typically CFC) does not degrade or affect the drug and its effect and, of course, in the illustrated embodiments, no additional propellant agent is required.

Many of the drugs presently administered by MDIs are concerned with bronchodilators and similar drugs for treating asthma, allergies and congestive disorders. However, it is becoming increasingly important to be able to treat other conditions (such as pneumonocystes carinii) by inhalation therapy. The reason for this is that drugs taken via the stomach are often destroyed by stomach secretions, or that which does get into the blood stream is taken out by the liver ("first pass metabolism"). In other cases, side effects can be severe. Some of these new drugs are difficult to micronise and, until now, they have been administered only be nebulization in hospitals, because a portable delivery method has not previously been available. Hospital nebulizers typically comprise gas blast devices in which small quantities of liquid product are added to large quantities of gas blasted under high pressure. Large gas cylinders are required for such apparatus, which is therefore distinctly non-portable. (Certainly in the sense of a pocket-sized device, or the like). Embodiments of the present invention may readily apply such drugs to readily portable devices and an important advantage is that such embodiments may be used immediately to administer drugs that are already tested and available for nebulizer application.

Another particularly useful advantage of the illustrated embodiments is that they may be used quite satisfactorily in an orientation. In contrast to this, existing sprayers, both the propellant type (e.g. CFC) and pump action type will work only in one (usually upright) orientation. It will be appreciated that patients can not always be relied upon to be in an upright position.

As suggested above in the foregoing description, embodiments of the present invention may include product container which are a least partially transparent, so that the level of the contents may be visually checked.

A further advantage of illustrated embodiments of the invention is that they may be constructed quite satisfactorily without the use of any elastomeric sealing members. This is in contrast to all known MDIs of which we are aware, which use resilient sealing members which may possibly degrade in contact with products to be dispensed, and/or in which extractable from the elastomers (e.g. rubbers) may leach into the products to be dispensed.

One reason why preferred embodiments of the invention can function well without the need for elastomeric seals is that the products are not stored under high pressure. High pressure exists only for a very short time, during the atomization cycle, Therefore, in the embodiments of FIGS. 1 and 2, for example, only a sealing cap or ring on the piston end portion 5 is required and, as mentioned above, this can be of PTFE or Nylon. In fact, it is both possible and desirable to manufacture the embodiments of FIGS. 1 and 2 entirely from stainless steel and approved plastics materials (e.g. polypropylene, PTFE, Nylon) which are entirely safe and non-reactive with the products to be dispensed.

If there is need for a seal at the connectors 12, this can be provided by a sealing ring or gasket of approved plastics (e.g. PTFE). Alternatively or additionally, the connectors such as 12 may include parts which screwthreadly engage, and at least one of which is of an approved plastic.

In the embodiment of FIG. 4, it is possible if desired, to employ elastomeric seals in the pressure pulse generator (not shown). This is because the product 70 is completely isolated from such seals by the flexible tube 75 and secondary liquid 78. The flexible tube 75 is of an approved plastics (e.g. polypropylene, PTFE, Nylon).

In the embodiment of FIGS. 1 and 2, a mechanical piston, urged by a strong spring, is used to create a pressure pulse which is applied to the liquid in the pressure chamber 4. Alternative means may be employed to produce such pressure pulses. For example, gas spring, electric motors, solenoids or other means may be employed.

Although above described embodiments of the invention utilize a liquid product which may typically comprise an aqueous solution of a drug, alternative fluid products may be used, For example, a fluid which is a suspension, emulsion or solution in water, alcohol or other liquid may be used.

As mentioned above, the illustrated embodiments of the invention may emit a spray at much less velocity than conventional MDIs. For example in a conventional CFC repellant MDI, the cloud or bolus of spray that is emitted may travel at a speed of the order of 30meters per second. Preferred embodiments of the present invention may release an equivalent amount of spray at a quarter of this speed. In fact it is possible to design embodiments of the present invention to match the optimum inhalation rate of the user at a figure of the order of 60 liters per minute.

The illustrated embodiments of the invention include means for metering a quantity-of fluid to be atomised. In alternative embodiments atomising devices may be provided with pre-metered quantities of fluid to be atomised. For example a strip of foil or plastics material (or other material) may contain individual pre-metered doses of liquid product and the strip could be punctured locally prior to or as part of a pressurising operation, following which the liquid is atomised to a fine spray. To this end, the strip may be pre-weakened at pre-determined locations, to promote correct rupturing of the strip material when required. Alternatively pre-metered doses of liquid product may be contained in individual capsules which are fed successively to a pressure chamber or other pressurizing location where the capsules are then ruptured. The strip material or capsules may be designed to rupture at a pre-determined pressure applied by the atomising device, such that a pressure release effect is created in the liquid product upon rupture.

All of the features disclosed in this specification (including any accompanying claims, abstract and drawings) and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in the specification (including any accompanying claims, abstract and drawings), or to any one novel one, or any novel combination, of the steps of any method or process so disclosed.

We claim:

1. A device for dispensing a metered quantity of fluid as a spray of droplets by discharging the metered quantity of fluid under pressure through an atomising means, comprising:

a chamber for containing said metered quantity of fluid at a first pressure;

an energy storage means for retaining and applying a predetermined amount of energy to said chamber so as to subject said metered quantity of fluid to a predetermined increase in pressure from said first pressure to a second pressure of at least 50 bar to permit discharge of said metered quantity of fluid from said chamber at said second pressure; and atomising means for atomising said fluid discharged from said chamber, said atomising means comprising an outlet aperture having a hydraulic diameter of 100 micrometers or less, whereby said fluid is atomized into droplets having a mean size suitable for inhalation into the lungs.

2. A device according to claim 1, further comprising:

a conduit connecting said chamber and said atomising means; and a valve mechanism for regulating the flow of fluid between said chamber and said atomising means.

3. A device according to claim 2 wherein said hydraulic diameter is of suitable size for formation of droplets having a mean size of less than 10 micrometers.

4. A device according to claim 2, wherein said valve mechanism comprises a pressure release valve.

5. A device according to claim 1, further comprising:

latching means to retain said energy storage means in a state retaining said predetermined amount of energy; and actuation means for releasing said predetermined amount of energy from said energy storage means.

6. A device according to claim 1, wherein said first pressure is substantially ambient pressure.

7. A device according to claim 1, wherein said outlet aperture has a hydraulic diameter of up to 50 micrometers.

8. A device according to claim 1, wherein said second pressure is in the range of approximately 100 bar to approximately 350 bar.

9. A device according to claim 8, wherein said hydraulic diameter is in the range of 1 to 12 micrometers.

10. A device according to claim 9, wherein said hydraulic diameter is in the range of 2 to 6 micrometers.

11. A device according to claim 1, wherein said energy storage means comprises a piston adapted to act directly on said chamber to pressurize said metered quantity of fluid.

12. A device according to claim 11, wherein said piston comprises a hollow channel in fluid communication with said chamber.

13. A device according to claim 12, further comprising:

a nor-return inlet valve for said chamber disposed within said channel.

14. A device according to claim 12, further comprising:

a fluid reservoir in fluid communication with said channel, wherein said piston extends from said fluid reservoir.

15. A device according to claim 1, wherein said hydraulic diameter is of suitable size for formation of droplets having a mean size of less than 10 micrometers.

16. A device according to claim 15, wherein said hydraulic diameter is of suitable size for formation of droplets having a mean size in the range of 2 to 6 micrometers.

17. A device according to claim 1, wherein said energy storage means comprises a pump having a piston and a spring, said chamber defined by a cylinder space in said pump beyond said piston.

18. A device according to claim 17, wherein said pump is provided with a latching mechanism whereby said pump can be held in a cocked state prior to release of the energy from said spring.

19. A device according to claim 1, further comprising:

a non return inlet valve in fluid communication with said chamber; and a non-return outlet valve in fluid communication with said chamber to permit repeated charge of fluid into said chamber and discharge of fluid from said chamber.

20. A device according to claim 1, further comprising:

a fluid reservoir in fluid communication with said chamber from which said chamber can be charged with fluid.

21. A device according to claim 20, wherein said fluid reservoir is removable.

22. A device according to claim 20, wherein said reservoir is collapsible.

23. A device according to claim 1, wherein said second pressure is in the range of approximately 300 bar to approximately 500 bar.

24. A device for dispensing a metered quantity of fluid as a spray of droplets by discharging the metered quantity of fluid under pressure through an atomising means, comprising:

a chamber for containing said metered quantity of fluid at a first pressure;

an energy storage means for retaining and applying a predetermined amount of energy to said chamber so as to subject said metered quantity of fluid to a predetermined increase in pressure from said first pressure to a second pressure of 50 bar or more to permit discharge of said metered quantity of fluid from said chamber at said second pressure; and atomising means for atomising said fluid from said chamber comprising an outlet aperture having a hydraulic diameter of 100 micrometers or less and configured so that said fluid forms a jet of fluid, and an impingement body located in the line of trajectory of said jet, said impingement body adapted to cause break up of said jet into a spray of droplets, said droplets having a mean size suitable for inhalation into the lungs.

25. A device according to claim 24, wherein said second pressure is in the range of approximately 100 bar to approximately 350 bar and wherein said hydraulic diameter is in the range of 1 to 12 micrometers.

26. A device according to claim 25, wherein said hydraulic diameter is in the range of 2 to 6 micrometers.

27. A device for dispensing a metered quantity of fluid as a spray of droplets by discharging the metered quantity of fluid under pressure through an atomising means, comprising:

a chamber for containing said metered quantity of fluid at a first pressure;

an energy storage means for retaining and applying a predetermined amount of energy to said chamber so as to subject said metered quantity of fluid to a predetermined increase in pressure from said first pressure to a second pressure of 50 bar or more to permit discharge of said metered quantity of fluid from said chamber at said second pressure; and atomising means for atomising said fluid from said chamber comprising a plurality of outlet apertures, each of said plurality of outlet apertures having a hydraulic diameter of 100 micrometers or less and configured so that said fluid forms a plurality of jets of fluid, said plurality of jets of fluid impinging upon one another to form a spray of droplets, said droplets having a mean size suitable for inhalation into the lungs.

28. A device according to claim 27, wherein said second pressure is in the range of approximately 100 bar to approximately 350 bar and wherein each of said plurality of outlet apertures has a hydraulic diameter in the range of 1 to 12 micrometers.

29. A device according to claim 28, wherein each of said plurality of outlet apertures has a hydraulic diameter in the range of 2 to 6 micrometers.

30. A device for dispensing a metered quantity of fluid as a spray of fine droplets by discharging the metered quantity of fluid under pressure through an atomizing means, comprising:

a chamber for containing said metered quantity of fluid at a first pressure;

an energy storage means for retaining and applying a predetermined amount of energy to said chamber so as to subject said metered quantity of fluid to a predetermined increase in pressure from said first pressure to a second pressure of at least about 100 bar to permit discharge of said metered quantity of fluid from said chamber at said second pressure; and atomizing means for atomizing said fluid discharged from said chamber, said atomizing means comprising an outlet aperture having a hydraulic diameter suitable for formation of atomized droplets having a mean size of less than 10 micrometers for inhalation into the lungs.

31. A device according to claim 30, wherein said hydraulic diameter is suitable for formation of atomized droplets having a mean size in the range of 2 to 6 micrometers.

32. A device for discharging a metered quantity of fluid as a spray of droplets by discharging the metered quantity of fluid under pressure through an atomising means, comprising:

a chamber for containing said metered quantity of fluid at a first pressure;

an energy storage means;

means for applying a predetermined amount of energy to said energy storage means;

means for releasing said predetermined amount of energy from said energy storage means to said chamber so as to subject said fluid to a predetermined increase in pressure to a second pressure and to initiate discharge of said fluid from said chamber; and atomising means for receiving said metered quantity of pressurized fluid from said chamber as a single discharge from said chamber, and for atomising said metered quantity of fluid, said atomising means comprising an outlet aperture having a hydraulic diameter of 100 micrometers or less whereby said fluid is atomized into droplets having a mean size suitable for inhalation into the lungs.

33. A device according to claim 32, wherein said second pressure is 50 bar or greater.

34. A device according to claim 33, wherein said hydraulic diameter is of suitable size for formation of droplets having a mean size of less than 10 micrometers.

35. A device according to claim 34, wherein said hydraulic diameter of said outlet aperture is 50 micrometers or less.

36. A device according to claim 34, wherein said hydraulic diameter is of suitable size for formation of droplets having a mean size in the range of 2 to 6 micrometers.

37. A device according to claim 31, wherein said second pressure is 100bar or greater.

38. A device according to claim 37, wherein said hydraulic diameter is of suitable size for formation of droplets having a mean size of less than 10 micrometers.

39. A device according to claim 32, wherein said hydraulic diameter is of suitable size for formation of droplets having a mean size of less than 10 micrometers.

40. A device according to 16 claim 39, wherein said hydraulic diameter is of suitable size for formation of droplets having a mean size in the range of 2 to 6 micrometers.

41. A device according to claim 32, further comprising:

a conduit connecting said chamber and said atomising means; and a valve mechanism for regulating the flow of fluid between said chamber and said atomising means.

42. A device according to claim 41, wherein said valve mechanism comprises a pressure release valve.

43. A device according to claim 32, further comprising:

a non return inlet valve in fluid communication with said chamber; and a non-return outlet valve in fluid communication with said chamber to permit repeated charge of fluid into said chamber and discharge of fluid from said chamber.

44. A device according to claim 24, further comprising:

a fluid reservoir in fluid communication with said chamber from which said chamber car be charged with fluid.

45. A device according to claim 44, wherein said fluid reservoir is removable.

46. A device according to claim 44, wherein said reservoir is collapsible.

47. A method of discharging a metered quantity of fluid as a spray of droplets by discharging the metered quantity of fluid under pressure through an atomising means, comprising the steps of:

providing said metered quantity of fluid in a chamber at which said fluid is held at a first pressure;

applying a predetermined amount of energy to an energy storage means;

releasing said predetermined amount of energy from said energy storage means to said chamber so as to subject said fluid to a predetermined increase in pressure to a second pressure and to initiate discharge of said fluid from said chamber; and discharging said metered quantity of pressurized fluid from said chamber as a single discharge from said chamber through an outlet aperture in the atomising means, said outlet aperture having a hydraulic diameter of 100 micrometers or less, thereby atomising said fluid into droplets having a mean size suitable for inhalation into the lungs.

48. A method according to claim 47, wherein said second pressure is from 50 to 500 bar and wherein said discharging step produces droplets having a mean size of less than 10 micrometers.

49. A method according to claim 45, wherein said energy storage means comprises a pump having a piston and a spring, said chamber defined by a cylinder space in said pump beyond said piston.

50. A method according to claim 49, wherein said pump is provided with a latching mechanism whereby said pump can be held in a cocked state prior to release of the energy from said spring.

51. A method according to claim 47, wherein said droplets have a mean size in the range of 1 to 12 micrometers.

52. A method according to claim 51, wherein said droplets have a mean size in the range of 2 to 6 micrometers.

53. A method of discharging a metered quantity of fluid as a spray of droplets by discharging the metered quantity of fluid under pressure through an atomising means, comprising the steps of:

providing said metered quantity of fluid in a chamber at which said fluid is held at a first pressure;

applying a predetermined amount of energy to an energy storage means;

releasing said predetermined amount of energy from said energy storage means to said chamber so as to subject said fluid to a predetermined increase in pressure from said first pressure to a second pressure of at least 50 bar; and discharging said fluid from said chamber through an outlet aperture in the atomising means, said outlet aperture having a hydraulic diameter of 100 micrometers or less, thereby atomising said fluid into droplets having a mean size suitable for inhalation into the lungs.

54. A method according to claim 53, wherein said droplets have a mean size in the range of 1 to 12 micrometers.

55. A metered dose inhaler for supplying fluid medicament to the lungs, comprising:

a chamber for containing a metered quantity of fluid medicament at a first pressure;

an energy storage means for retaining and applying a predetermined amount of energy to said chamber so as to subject said metered quantity to a predetermined increase in pressure from said first pressure to a second pressure of at least 50 bar to permit discharge of said metered quantity from said chamber at said second pressure, said energy storage means comprising a piston adapted to act directly on said chamber to pressurize said metered quantity, a spring, and a latching mechanism whereby said energy storage means can be held in a cocked state prior to release of the energy from said spring; and atomising means for atomising said metered quantity discharged from said chamber, said atomising means comprising a first outlet aperture having a hydraulic diameter of 100 micrometers or less.

56. A metered dose inhaler according to claim 55, further comprising:

a non-return inlet valve, wherein said piston comprises a hollow channel in fluid communication with said chamber, said non-return inlet valve disposed within said channel; and a fluid reservoir in fluid communication with said channel, wherein said piston extends from said fluid reservoir.

57. A metered dose inhaler according to claim 56, wherein said latching mechanism is released to initiate discharge of said metered quantity from said chamber at said second pressure, wherein said second pressure is in excess of 100 bar.

58. A metered dose inhaler according to claim 56, wherein said atomising means further comprises:

a second outlet aperture, wherein a first jet of said metered quantity is discharged through said first outlet aperture and a second jet of said metered quantity is discharged through said second outlet aperture, said first jet and said second jet impinging upon one another to form a spray of droplets.

59. A-metered dose inhaler according to claim 56, wherein said second pressure is in excess of 100 bar.

60. A metered dose inhaler according to claim 55, wherein said latching mechanism is released to initiate discharge of said metered quantity from said chamber at said second pressure.

61. A metered dose inhaler according to claim 60, wherein the second pressure is in excess of 100 bar.

62. A metered dose inhaler according to claim 60, wherein said atomising means further comprises:

a second outlet aperture, wherein a first jet of said metered quantity is discharged through said first outlet, aperture and a second jet of said metered quantity is discharged through said second outlet aperture, said first jet and said second jet impinging upon one another to form a spray of droplets.

63. A metered dose inhaler according to claim 55, wherein said second pressure is in excess of 100 bar.

64. A metered dose inhaler according to claim 55, wherein said atomising means further comprises:

a second outlet aperture, wherein a first jet of said metered quantity is discharged through said first outlet aperture and a second jet of said metered quantity is discharged through said second outlet aperture, said first jet and said second jet impinging upon one another to form a spray of droplets.

65. A device for dispensing a metered quantity of fluid as a spray of droplets by discharging the metered quantity of fluid under pressure through an atomising means, comprising:

a chamber for containing said metered quantity of fluid at a first pressure;

an energy storage means for retaining and applying a predetermined amount of energy to said chamber so as to subject said metered quantity of fluid to a predetermined increase in pressure from said first pressure to a second pressure of at least 50 bar to permit discharge of said metered quantity of fluid from said chamber at said second pressure; and atomising means for atomising said fluid discharged from said chamber, said atomising means comprising an outlet aperture having a hydraulic diameter of suitable size for formation of droplets having a mean size of less than 10 micrometers for inhalation into the lungs.

66. A device according to claim 65, further comprising:

a conduit connecting said chamber and said atomising means; and a valve mechanism for regulating the flow of fluid between said chamber and said atomising means.

67. A device according to claim 65, further comprising:

latching means to retain said energy storage means in a state retaining said predetermined amount of energy; and actuation means for releasing said predetermined amount of energy from said energy storage means.

68. A device according to claim 65, wherein said first pressure is substantially ambient pressure.

69. A device according to claim 65, wherein said second pressure is in the range of approximately 100 bar to approximately 350 bar.

70. A device according to claim 65, wherein said energy storage means comprises a piston adapted to act directly on said chamber to pressurize said metered quantity of fluid.

71. A device according to claim 70, wherein said piston comprises a hollow channel in fluid communication with said chamber.

72. A device according to claim 71, further comprising:

a non-return inlet valve for said chamber disposed within said channel.

73. A device according to claim 71, further comprising:

a fluid reservoir in fluid communication with said channel, wherein said piston extends from said fluid reservoir.

74. A device according to claim 65, wherein said second pressure is in the range of approximately 300 bar to approximately 500 bar.

75. A method of discharging a metered quantity of fluid as a spray of droplets by discharging the metered quantity of fluid under pressure through an atomising means, comprising the steps of:

providing said metered quantity of fluid in a chamber at which said fluid is held at a first pressure;

applying a predetermined amount of energy to an energy storage means;

releasing said predetermined amount of energy from said energy storage means to said chamber so as to subject said fluid to a predetermined increase in pressure from said first pressure to a second pressure of at least 50 bar; and discharging said fluid from said chamber through an outlet aperture in the atomising means, said outlet aperture having a hydraulic diameter of suitable size for formation of droplets having a mean size of less than 10 micrometers, thereby atomising said fluid into droplets having a mean size suitable for inhalation into the lungs.

76. A device for discharging a metered quantity of fluid as a spray of droplets by discharging the metered quantity of fluid under pressure through an atomising means, comprising:

a chamber for containing said metered quantity of fluid at a first pressure;

an energy storage means;

means for applying a predetermined amount of energy to said energy storage means;

means for releasing said predetermined amount of energy from said energy storage means to said chamber so as to subject said fluid to a predetermined increase in pressure to a second pressure to permit discharge of said metered quantity of fluid from said chamber at said second pressure; and atomising means for receiving said metered quantity of pressurized fluid from said chamber, and for atomising said metered quantity of fluid, said atomising means comprising an outlet aperture having a hydraulic diameter of 100 micrometers or less whereby said fluid is atomized into droplets having a mean size suitable for inhalation into the lungs.

* * * * *

UNITED STATES PATENT AND TRADEMARK OFFICE
CERTIFICATE OF CORRECTION

PATENT NO.  : 5,497,944
DATED       : March 12, 1996
INVENTOR(S) : Weston, et al.

It is certified that error appears in the above-indentified patent and that said Letters Patent is hereby corrected as shown below:

Column 20, line 52, claim 49, line 1, please replace "45" with --47--.

Signed and Sealed this

Fifteenth Day of October, 1996

Attest:

BRUCE LEHMAN

*Attesting Officer*  *Commissioner of Patents and Trademarks*